United States Patent [19]

Nanna et al.

[11] Patent Number: 5,552,890
[45] Date of Patent: Sep. 3, 1996

[54] GLOSS MEASUREMENT SYSTEM

[75] Inventors: Frank P. Nanna, Crystal Lake; John Jereb, Dundee, both of Ill.

[73] Assignee: Tricor Systems, Inc., Elgin, Ill.

[21] Appl. No.: 519,622

[22] Filed: Aug. 25, 1995

Related U.S. Application Data

[63] Continuation of Ser. No. 229,617, Apr. 19, 1994, abandoned.

[51] Int. Cl.$^6$ .................................................. G01J 4/00
[52] U.S. Cl. ....................... 356/369; 356/446; 356/448; 348/128
[58] Field of Search ................................ 356/369, 364, 356/445, 446, 447, 448, 371, 322, 327; 250/571, 572, 559, 562, 225; 348/128; 382/8, 52

[56] References Cited

U.S. PATENT DOCUMENTS

| | | | |
|---|---|---|---|
| 3,904,293 | 9/1975 | Gee | 356/448 |
| 3,992,571 | 11/1976 | Garlick et al. | 356/365 |
| 3,999,864 | 12/1976 | Mutter | 356/212 |
| 4,218,144 | 8/1980 | Whitehouse et al. | 356/445 |
| 4,613,235 | 9/1986 | Suga | 356/446 |
| 4,746,805 | 5/1988 | Stapleton | 250/571 |
| 4,750,140 | 6/1988 | Asano et al. | 364/526 |
| 4,830,504 | 5/1989 | Frohardt et al. | 356/448 |
| 4,853,777 | 8/1989 | Hupp | 348/128 |
| 4,886,355 | 12/1989 | Keane | 356/73 |
| 4,931,657 | 6/1990 | Houston et al. | 356/369 |
| 4,945,253 | 7/1990 | Frohardt | 250/571 |
| 5,173,750 | 12/1992 | Laukaitis | 356/445 |
| 5,189,490 | 2/1993 | Shetty et al. | 356/371 |
| 5,235,434 | 8/1993 | Wober | 382/52 |

*Primary Examiner*—Hoa Q. Pham
*Attorney, Agent, or Firm*—Marshall, O'Toole, Gerstein, Murray & Borun

[57] ABSTRACT

A gloss measurement system for optically measuring gloss based solely on the specular light reflected from an object. Two polarizing filters, each oriented 90 degrees with respect to each other, are used in order to separate the diffuse or color reflection component from the specular or gloss reflection component. Two images are digitized sequentially using each of the two polarizing filters. The images are subtracted from each other on a pixel by pixel basis and the resulting image contains only specular or gloss reflections. This resulting image is then statistically manipulated in order to group gloss pixels by magnitude. This grouping results in a gloss profile which is a direct indicator of surface gloss.

25 Claims, 22 Drawing Sheets

GLOSS MEASUREMENT SYSTEM

This is a Continuation of U.S. application Ser. No. 08/229,617, filed Apr. 19, 1994, now abandoned.

TECHNICAL FIELD

The present invention relates generally to a method and apparatus for measuring the gloss of an object and more specifically to the accurate measurement and analysis of an object's gloss level regardless of the object's shape, texture, or color.

BACKGROUND OF THE INVENTION

Light reflecting from an object's surface at an angle of reflection to the surface equal to the angle of incidence to the surface is known as the specular angle of reflection, or simply specular reflection or the specular direction. Gloss is associated with the capacity of a surface to reflect more light in the specular direction as compared to other directions. Material surfaces that are not perfectly smooth are assumed to have a microscopic level of detail which consists of a statistically large distribution of microfacets.

Most light reflected from a material surface arises from the following four phenomena:

(a) Light waves which specularly reflect off a planar surface significantly larger than the wavelength;

(b) Light waves which go through at least two multiple specular reflections amongst multiple microfacets;

(c) Light waves which penetrate into the top layer of the material surface, multiply refract, then are reflected back out; and (d) Light waves which diffract from interfaces with surface detail about the same size or smaller than the wavelength of the incident light.

The component of reflection which arises from phenomenon (a) is called the specular component of reflection. The angle that the incident light wave intercepts the test surface normal is called the specular angle of incidence. The component of reflection arising from phenomena (b) through (d) is called the diffuse component of reflection. If a beam of unpolarized light strikes a non-metallic surface at a specific angle, the reflected beam will be partially or completely linearly polarized. The degree of polarization depends upon the incident angle and the refraction index of the reflecting surface. The angle of which the degree of polarization is 100% is defined as the maximum polarization or Brewster angle.

Unpolarized light has equal magnitude polarization components in all directions. However, unpolarized light becomes partially polarized upon specular reflection. It is known that the polarization component perpendicular to the specular plane is larger than the magnitude of the polarization component parallel to the specular plane. It also is known that for a single specular reflection at an oblique angle, the magnitude of the perpendicular polarization component is not as attenuated as the magnitude of the parallel polarization component.

Over many years various equipments and/or methodologies have been devised or proposed to measure the visual gloss of various items. Reference may be made, for instance, to the following U.S. Pat. Nos. of interest: 3,999,864; 4,613,235; 4,746,805; 4,750,140; 4,886,355; 4,945,253.

Mutter U.S. Pat. No. 3,999,864 shows a gloss measuring instrument which transmits multiple beams of light to a fiber optic bundle to direct the light towards a sample at various angles of incidence. Light reflected from the sample is provided to a photodetector at different wavelengths that are a function of the angle of incidence of the light onto the sample. The photodetector develops signals indicative of the intensities of the wavelengths of light reflected from the surface sample which, along with a gloss standard, are used to compute a gloss measurement of the sample. Suga U.S. Pat. No. 4,613,235 discloses a gloss measuring system directing parallel light rays against a surface to measure gloss at a particular angle of incidence and corresponding angle of reflection. The central portion of the reflected light is blocked so that only the light diffusedly reflected from the surface at the angle of reflection is used to determine the gloss of the surface. Stapleton U.S. Pat. No. 4,746,805 discloses a gloss meter which includes a light source illuminating a sample surface and a motor driven chopper blade for interrupting the illumination and causing a reflection of the edge of the blade in the finish of the surface. The detector output is analyzed to determine the rate of change of the detector signal which is integrated to determine the gloss of the surface. Asano, et al. U.S. Pat. No. 4,750,140 shows a method and apparatus for determining glossiness of a surface based on the visible feeling by the light reflection intensity distribution of a surface. The gloss of the surface is determined by measuring the ratio of the specular reflection intensity to the total reflection intensity of the surface, plotting the measured ratio in relation to a predetermined curve, and determining which of the predefined curve sections the measured ratio corresponds to. Keane U.S. Pat. No. 4,886,355 shows an instrument for measuring gloss by detecting light specularly reflected from an illuminated sample surface. The detected intensity of the specular reflection provides an indication of the gloss of the sample surface. Frohardt U.S. Pat. No. 4,945,253 shows a device which optically measures the gloss of a surface using diffused light reflected from the surface.

None of the prior techniques has proven successful when measuring the gloss of an irregularly shaped substance of varying colors. In fact, manufacturers of present day gloss measuring equipments do acknowledge this technology limitation and continue to seek a solution to this longstanding problem.

SUMMARY OF THE INVENTION

In accordance with the present invention there is provided a method and apparatus to accurately and reliably measure a surface's ability to reflect light in a mirror like manner and thereby provide a measure of the surface's gloss level. The present invention includes a CCD camera sensor to evaluate a sample within a controlled environment (i.e. a chamber) with a closely monitored, unpolarized, broad band light source illuminating the sample's surface. The light source within the chamber assures assessment of a sample to be consistent over time by correcting for any variations in the light level. In one aspect of the invention the specular reflections are separated from the inherent diffuse reflections by polarizing filters and image processing to provide the gloss image. Upon separation of the reflection components only the specular reflection, which is the component that gives a surface its mirror quality, is statistically evaluated. Color becomes a non-factor in the gloss measurement by eliminating the diffuse characteristics of a sample.

Statistical manipulation of the resulting gloss image enables differentiation between illuminated and shadowed areas. Shadowed areas should not and are not included in the gloss analysis. Calculations are performed on the illuminated areas of the sample and the results are classified into groups based on amplitude. This statistical grouping method allows texture to be a non-factor in the gloss analysis.

In accordance with the method aspect of the present invention, there is provided a method of optically measuring the gloss of an object utilizing the specular reflection component of unpolarized, broad band light reflected from the object, wherein the object is illuminated with a light source directed at an oblique angle to the object. A perpendicular polarized filter is provided at the oblique angle to detect a first amount of specular reflection of light from the object including a perpendicular polarization component and diffuse components. A parallel polarized filter is then provided at the oblique angle to detect a second amount of specular reflection of light from the object including a parallel polarization component and diffuse components, wherein the amount of the parallel polarization component is substantially less than the amount of the perpendicular polarization component. The difference between the first and second amounts of specular reflection is obtained to derive a third amount of specular reflection corresponding essentially to the perpendicular polarization component to provide a gloss image of the object. The absolute average gloss of the object is obtained from the derived gloss image by selecting a location within the gloss image, deriving the absolute sum of the gloss image pixels within the selected gloss image location, deriving the number of the gloss image pixels within the selected gloss image location, and dividing the derived absolute sum of the gloss image pixels by the number of the gloss image pixels.

In accordance with the principles of the invention, there is provided an accurate and reliable measure of a surface's gloss value, thereby achieving an objective measure of the gloss value which previously amounted to a subjective measure in the prior art. In addition, the present invention can accurately and reliably measure the gloss of an irregularly shaped substance of varying colors because the diffuse characteristics of a sample are eliminated in the technique of the present invention. Texture is also eliminated as a factor in accordance with the technique of the present invention.

As will be more particularly described hereinafter, the present invention also includes several features which provide significant advantages in system utility, accuracy, and reliability when compared to the prior art, namely:

1. The use of polarizing filters to generate two images which are subtracted on an absolute pixel by pixel basis and corrected for falloff. The resulting difference image is considered to be a gloss image;
2. A CCD camera to measure gloss with multi-shutter speed capability in order to gain dynamic range;
3. A sample table with height adjustment to maintain measuring geometry regardless of sample height;
4. A monitored light source that senses changes in light level relative to the level measured during calibration so as to correct absolute gloss calibration;
5. The derivation of a gloss image to be used in conjunction with gloss measurements;
6. A pure difference image used to correct for image falloff characteristics;
7. Differentiating between shadowed areas from those areas containing specular reflections by using a threshold limitation;
8. Grouping gloss pixels by amplitude in order to generate a Gloss Profile Summary;
9. Correcting for errors during operation of the gloss measurement by utilizing calibration standards and calibration routines, including corrections for black level offsets, gain factors and geometry changes;
10. Utilizing a light source and camera pattern correction algorithm to provide illumination/sensing field flattening, thus improving system accuracy; and
11. Method and apparatus permitting measuring an object's gloss regardless of shape, texture and color.

In a constructed embodiment of the invention, a camera/filter assembly is mounted at a 60° incident angle for samples having an index of refraction of approximately 1.7. The apparatus includes means for changing the incidence angle depending on the sample index of refraction. The index of refraction of the sample will determine the optimum angle of incident in order to optimize the maximum polarization characteristics of a particular sample.

BRIEF DESCRIPTION OF THE DRAWINGS

These and other features and advantages will become more apparent from a detailed consideration of the invention when taken in conjunction with the drawings in which.

DESCRIPTION OF THE PREFERRED EMBODIMENTS

Figure 1:
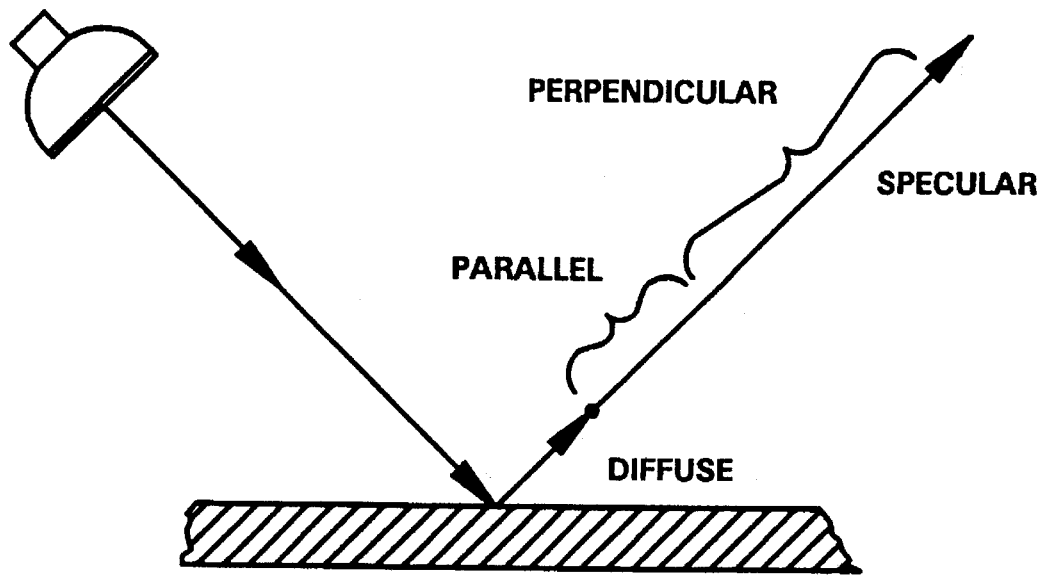
FIG. 1 is a schematic illustration useful in explaining the present invention and depicting reflected light from a surface represented as three components.

Initially, a description of the principles underlying the present invention will be presented, followed by a detailed description of the preferred embodiment of a gloss measurement system operating in accordance with the invention. As previously indicated, for a single specular reflection at an oblique angle, the magnitude of the perpendicular polarization component is much larger than the magnitude of the parallel polarization component. The reflected light from a surface can be represented for instance as the vector sum of an unpolarized component, the polarized component, and the diffuse component, as illustrated in FIG. 1.

Figure 2:
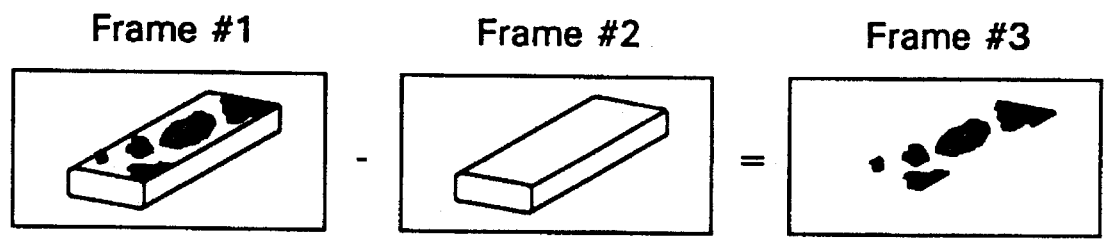
FIG. 2 is a schematic illustration of the measurement technique utilizing the three components of FIG. 1 according to the invention.

By utilizing two polarizing filters rotated 90° from each other, the parallel and perpendicular specular components can be separated and measured. Referring to FIG. 2, there is illustrated Frame #1 representing the information acquired by a first perpendicular polarizing filter position to eliminate the parallel component and one-half of the diffuse components. The diffuse component is comprised of light equally polarized in all directions and therefore, when a polarizing filter is used one-half of the diffuse light will be filtered out.

The same techniques hold for acquiring Frame #2 in that, the second parallel polarizing filter position will eliminate the perpendicular component and one-half of the diffuse components. The subtraction or difference in the information between the two frames, Frame #2 from Frame #1, represents only the specular component of the reflected light, i.e., Frame #3 when the perpendicular component is much larger than the parallel component.

Frame #3 represents the gloss image used to calculate an absolute average gloss. The absolute average gloss calculation is applied to a user specified location within the gloss image. Absolute average gloss is calculated by finding the average absolute pixel value for the pixels above the user specified threshold value, and is derived from the absolute sum of the pixels above the threshold divided by the number of pixels above the threshold (i.e. statistical average). A Gloss Profile Summary is obtained by the grouping of pixels into user specified group sizes based on amplitude. An Absolute Average calculation is applied to the pixels within each of these groups, as well as, standard deviation.

Figure 3:
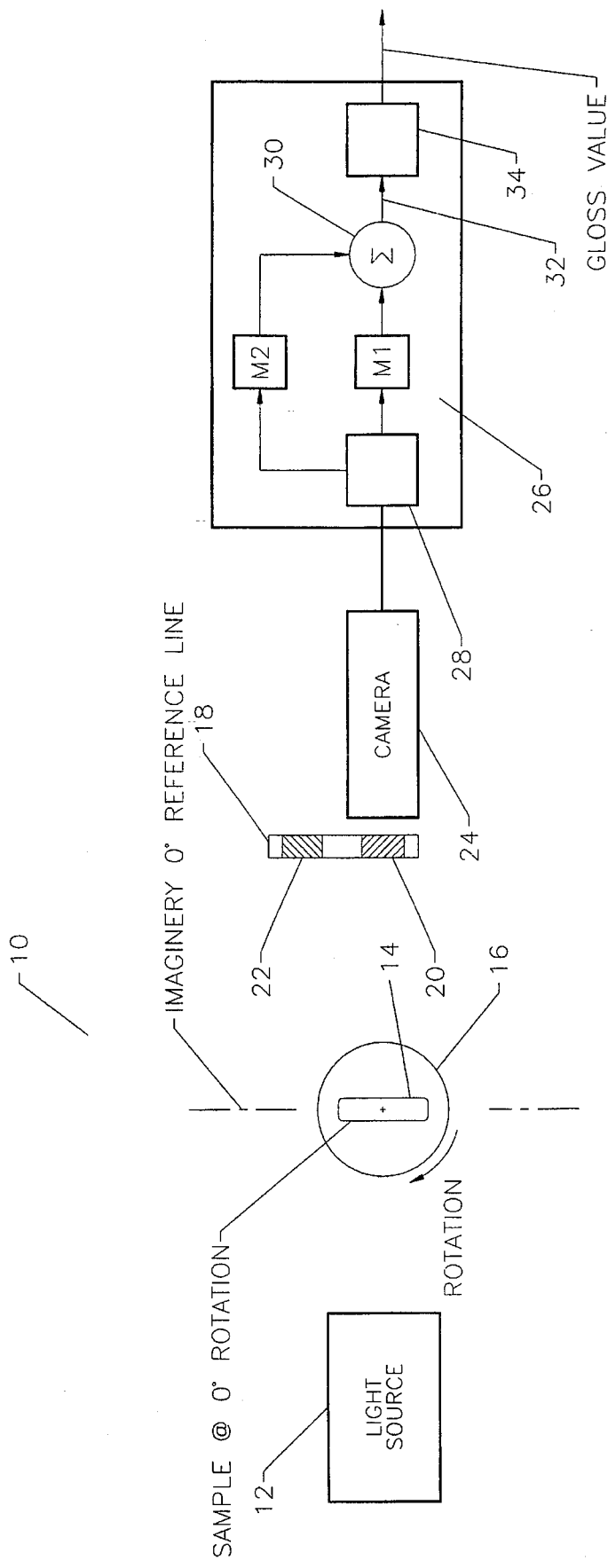
FIG. 3 is a schematic block diagram illustrating a gloss measurement system in accordance with the present invention.

FIG. 3 is a schematic diagram illustrating a gloss measurement system 10 incorporating the principles of the present invention. The gloss measurement system 10 includes a light source 12 which illuminates a sample 14 located on a sample table 16 which is rotatable relative to the light source 12. A movable filter mechanism 18 includes two polarizing filters 20, 22 mounted on the front of a video camera 24. Polarizing filter 20 is positioned to receive the perpendicular reflection and polarizing filter 22 is positioned to receive the parallel specular reflection resulting from the light from light source 12 being directed at an oblique incident angle to the sample 14.

Accordingly, during operation the video camera 24 receives light from the sample 14 and the sample table 16 and is filtered by polarizing filter 20 to produce an image represented by the Frame #1 of FIG. 2 and which image is delivered to an image processor 26. The image processor 26 includes a digitizer 28 which digitizes the image of Frame #1 and stores the digitized Frame #1 in a first digital memory M1. The filter mechanism 18 is then moved so that the second polarizing filter 22 is disposed in front of the video camera 20. The video camera 20 then receives light reflected from the sample 14 and sample table 16 and is filtered by the second polarizing filter 22 to produce a second image represented by Frame #2 as shown in FIG. 2, and which Frame #2 image is sent to the image processor 26, digitized, in the digitizer 28 and stored in a second digital memory M2.

The image processor 26 also includes a summer 30 which subtracts each pixel of the Frame #2 image stored in the memory M2 from the corresponding pixel of the Frame #1 image stored in the memory M1 to produce a gloss image on line 32, each pixel of which is indicative of the specular component of light reflected from a finite area of the sample 14 on the sample table 16. The gloss image is then delivered to a microprocessor 34.

In order to quantify the glossiness of the sample 14, the microprocessor 34 statistically groups the gloss image pixels according to gloss levels (which correspond to pixel brightness) which, in effect, groups similarly glossy regions together. The microprocessor 34 then averages the brightest N (a variable chosen by the user) percentage of the gloss image pixels together to calculate the overall gloss value (or glossiness) of the sample 14. This grouping technique virtually assures that portions of the sample 14 with similar geometry are being grouped together and provides a consistent measurement of gloss. Furthermore, the gloss value produced by the microprocessor 34 is traceable to a reference set of gloss values input by the user or stored in a memory associated with the image processor 26 to provide a comparative measurement of the glossiness of the sample 14. Accordingly, the output of the microprocessor 34 represents the gloss value of the sample 14.

Figure 4:
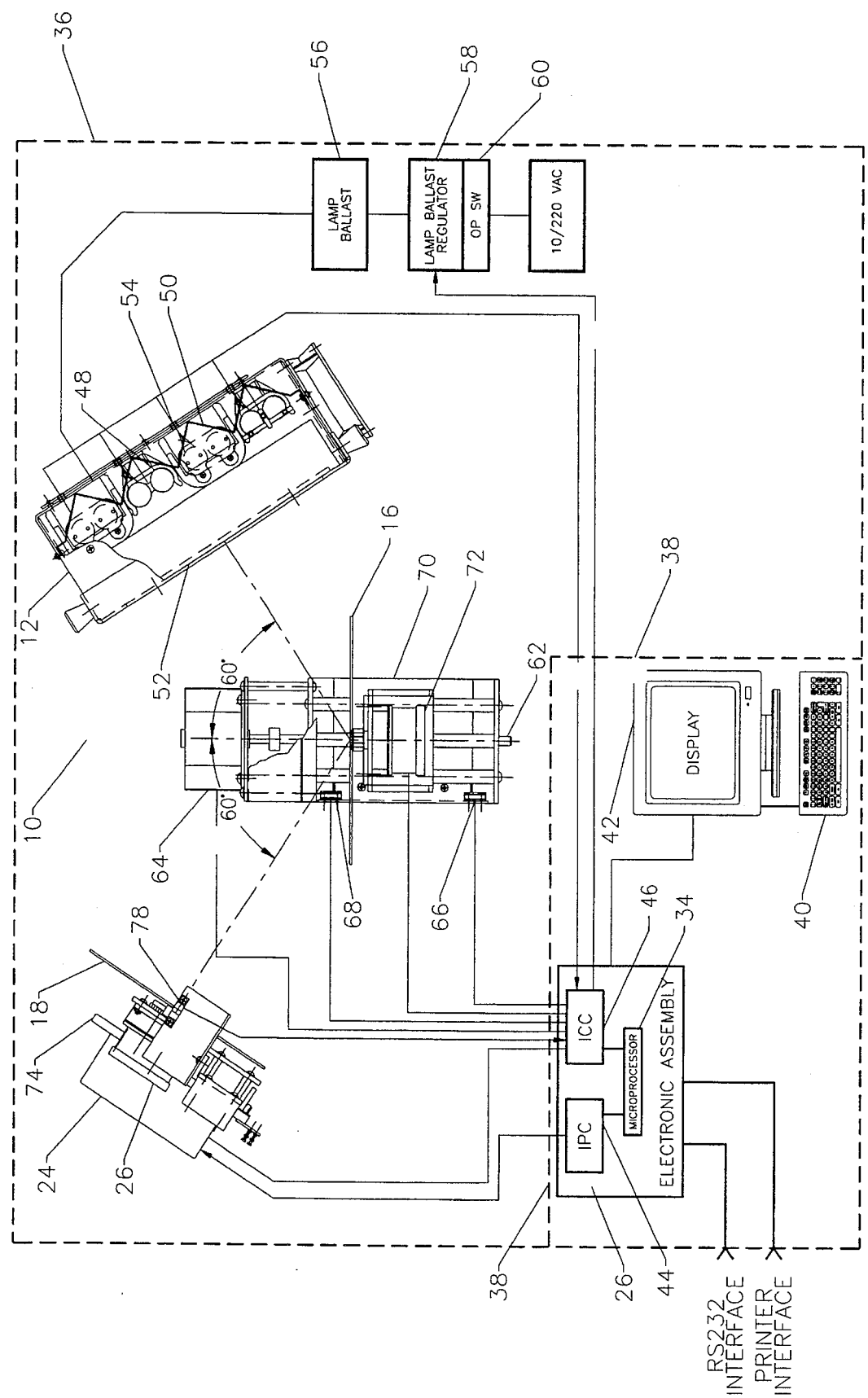
FIG. 4 is a schematic diagram illustrating apparatus according to the invention including a test chamber assembly containing an adjustable sample table, a light source, and a filter/light detector assembly.

Shown in FIG. 4 is a preferred embodiment of a gloss measurement system 10 according to the present invention. The gloss measurement system 10 is broadly grouped into two major assemblies, i.e., an enclosed test chamber 36 and a computer system 38. Within the enclosed test chamber 36 is the light source 12, the rotatable and height adjustable sample table 16, the video camera 24 and the movable filter mechanism 18 in the form of a filter wheel assembly. The computer system 38 includes the image processor assembly 26, keyboard 40, display 42, parallel printer interface, RS-232 interface, VGA interface, and a storage medium (not shown). The image processor 26 can include the items shown in FIG. 3, as well as an image-processing circuit 44, and an analog/digital interface circuit 46. It is understood that some functions shown in FIG. 3 may be performed in software, as explained hereinafter.

Prior to describing the operational sequence of the system, a brief description of each of these elements will be given. Because of the large acceptance angle or field of view of the video camera 24, the light source 12 is of significant size. The light source 12 is comprised of four U-shaped high intensity fluorescent lamps 48 providing an unpolarized, broad light source. These lamps are bracketed by a reflector assembly 50 to provide field flattening of the illumination pattern. In addition to the reflectors 50, a diffuser 52 is located on the front of the light source assembly to additionally flatten the field. The light source 12 is constructed to provide a flat illumination across the complete diffuser area.

The light source also includes four photodiodes 54 to monitor the intensity of each of the fluorescent bulbs. The photodiode output signals are respectively coupled back to the interface circuit card 46. These photodiodes 54 are used for several purposes. First, they are employed to provide the absolute intensity of the lamps 48 so that any variations during operation can be corrected for in the processing algorithm. Secondly, the feedback is used to identify aging problems or lamp failures. Because of the high brightness and power requirements of the light source 12, cooling air is passed through the assembly to achieve stable thermal operation. The fluorescent lamps 48 are powered by a solid state, high frequency lamp ballast 56. Standard 60-cycle ballasts cannot be employed in this application due to the high ripple content and light modulation resulting from the low line frequency. By using the solid-state ballast 56 operating above 20,000 Hz, light modulation is eliminated by the integrating lag time of the fluorescent phosphor. The lamp ballast is also buffered by an additional regulated DC power supply 58 and an optical switch 60. The PC power supply provides additional 60 Hertz line attenuation. The optical switch 60 is used to turn the light source 12 on and off during operation of the system. Various aspects of operation, i.e. black level monitoring, must be performed with the light source off. Therefore, the optical switch 60 permits this mode of operation.

The sample table assembly 70 is used to permit height adjustment and rotation of the test sample 14 on table 16. Height adjustment is required for proper operation of the unit based on maintaining the sixty degree incident angle technology. A screw drive assembly 62, coupled to a stepping motor 64 and to table 16, is used to adjust the sample height over a range of 0 to three inches. The stepper motor 64 is controlled by the interface circuit 46. Respective limit switches 66, 68 are located at the top and bottom of the assembly so that accurate position information can be obtained and maintained during operation. Upon initialization of the system, the stepper motor 64 will be commanded to move the connected table 16 to the upper limit switch 68. Once in this position, the system is zeroed and any movement from this point is recorded and maintained. Therefore, if a one-inch sample is inserted on the table 16, the operator would command the system to lower the sample by one inch thus maintaining the desired 60° incident angle technology. In addition to the height adjustment, rotation of the sample is also provided. A second stepper motor 72 is located beneath the table 16. Stepper motor 72 is commanded to specific angular changes or displacements based on operator command through the interface circuit 46. This permits gloss measurements to be performed in a 360° format around the sample.

The next major assembly of the enclosed test chamber 36 is the CCD video camera 24 and a polarizing filter wheel assembly 74. The reflected energy from the sample is recorded via a black and white solid-state CCD camera 24. Two polarizers 20, 22, rotated by 90° from each other, are located on the polarizer filter wheel 18 forming a part of the filter wheel assembly 74. The filter wheel 18 is rotated by the filter wheel assembly 74 about a center axis to position each filter 20, 22 in front of the video camera 24 to record the parallel and perpendicular specular images of the sample 14. An optical sensor in the filter wheel assembly 74 is located on the filter wheel 18 to accurately sense the first filter position. A stepper motor 78 is used to accurately position the filter wheel 18 via commands from the computer system 38 and the interface circuit 46. In addition, the interface circuit 46 supplies digital command interface signals to the CCD camera 24 to control an electronic shutter. Eight shutter speeds are available, thus increasing the dynamic range of the system significantly.

The image-processor 44 includes an analog to digital converter that converts and stores the analog video information from the CCD camera to 8-bit digital values to provide a gloss image on line 32 (see FIG. 3) that is processed by the microprocessor 34 under control of the gloss analytical software.

The following will detail the software programming and the analytical algorithms that are processed during the gloss measurement calculation.

Figure 5A:
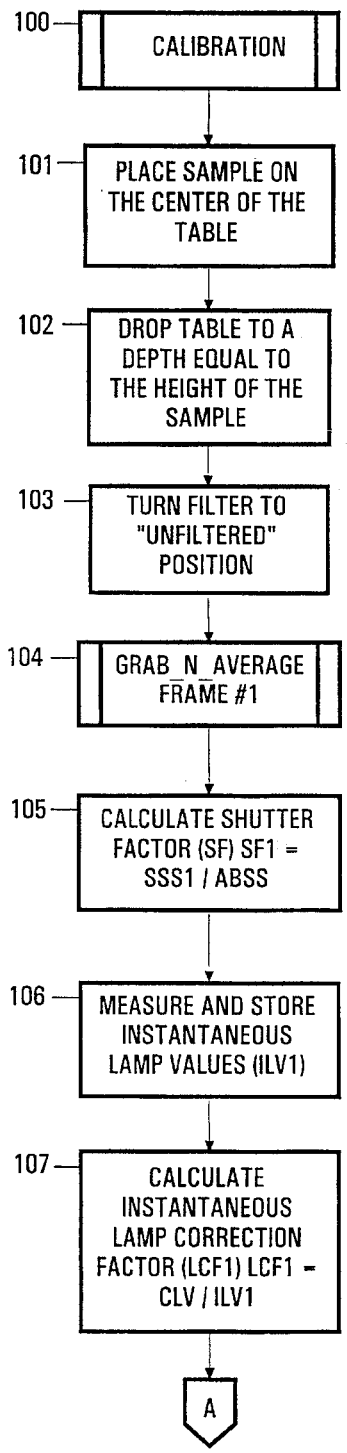
FIG. 5a–5r is a functional flow chart of the program for controlling the apparatus illustrated in FIGS. 3 and 4 and performing the gloss measurement analysis in accordance with the present invention.
Figure 5B:
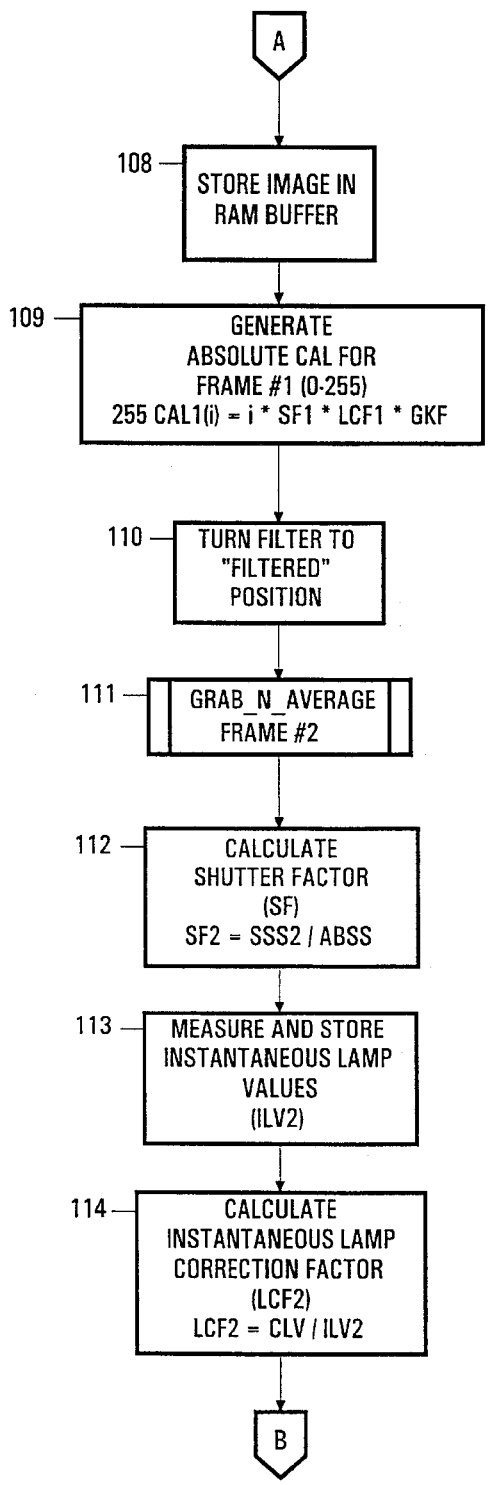
Figure 5C:
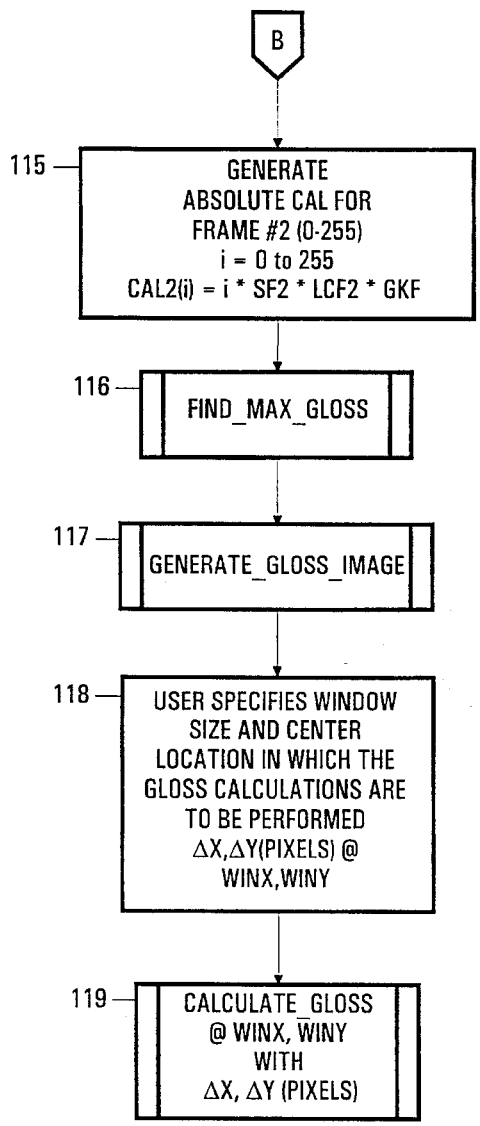
Figure 5D:
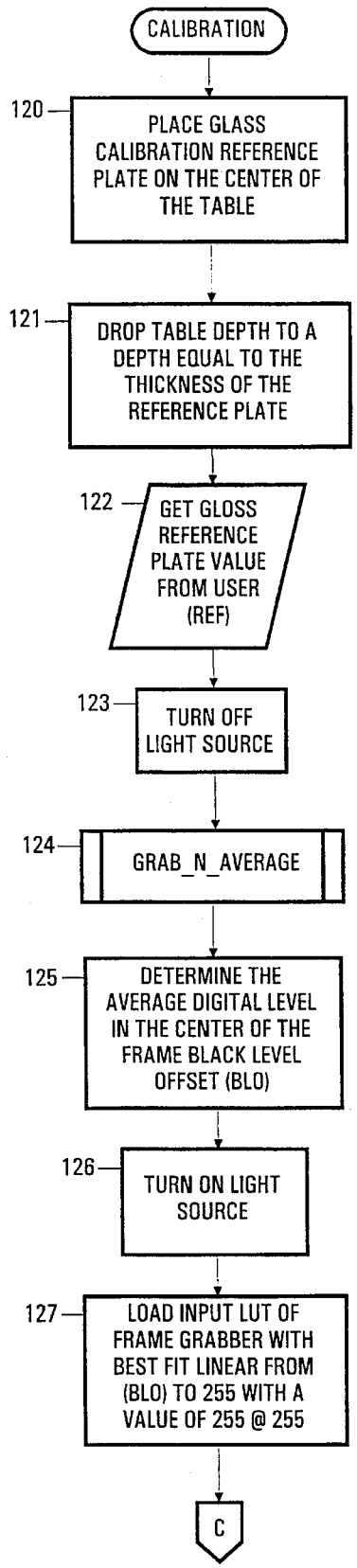
Figure 5E:
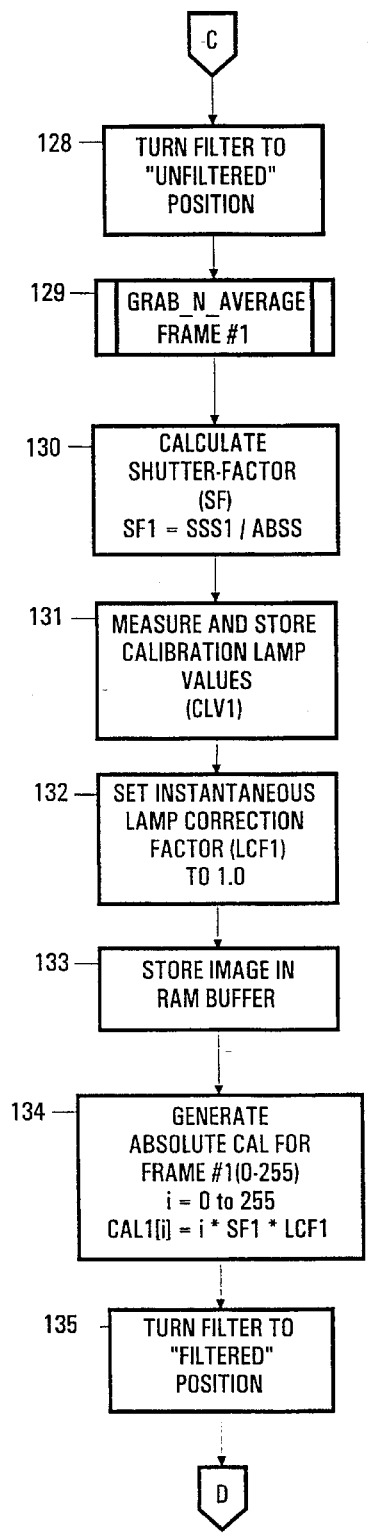
Figure 5F:
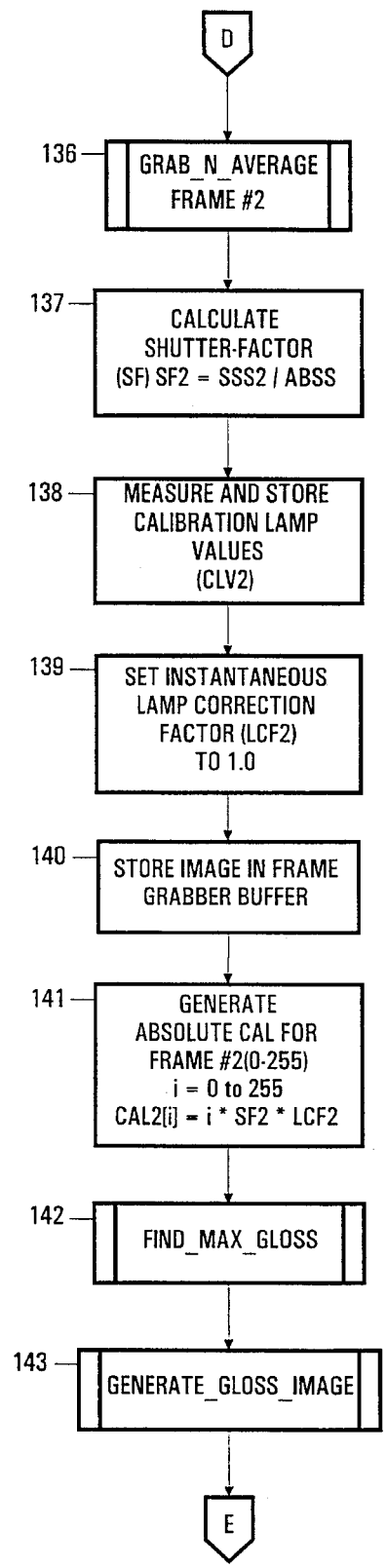
Figure 5G:
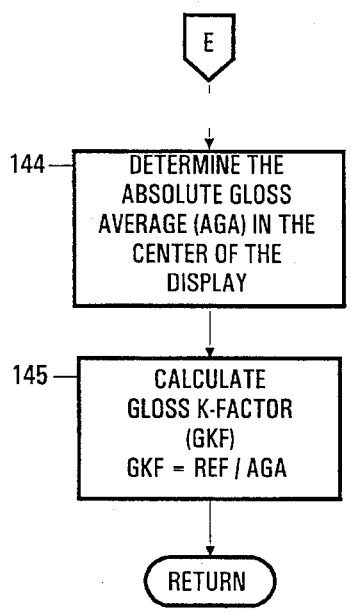
Figure 5H:
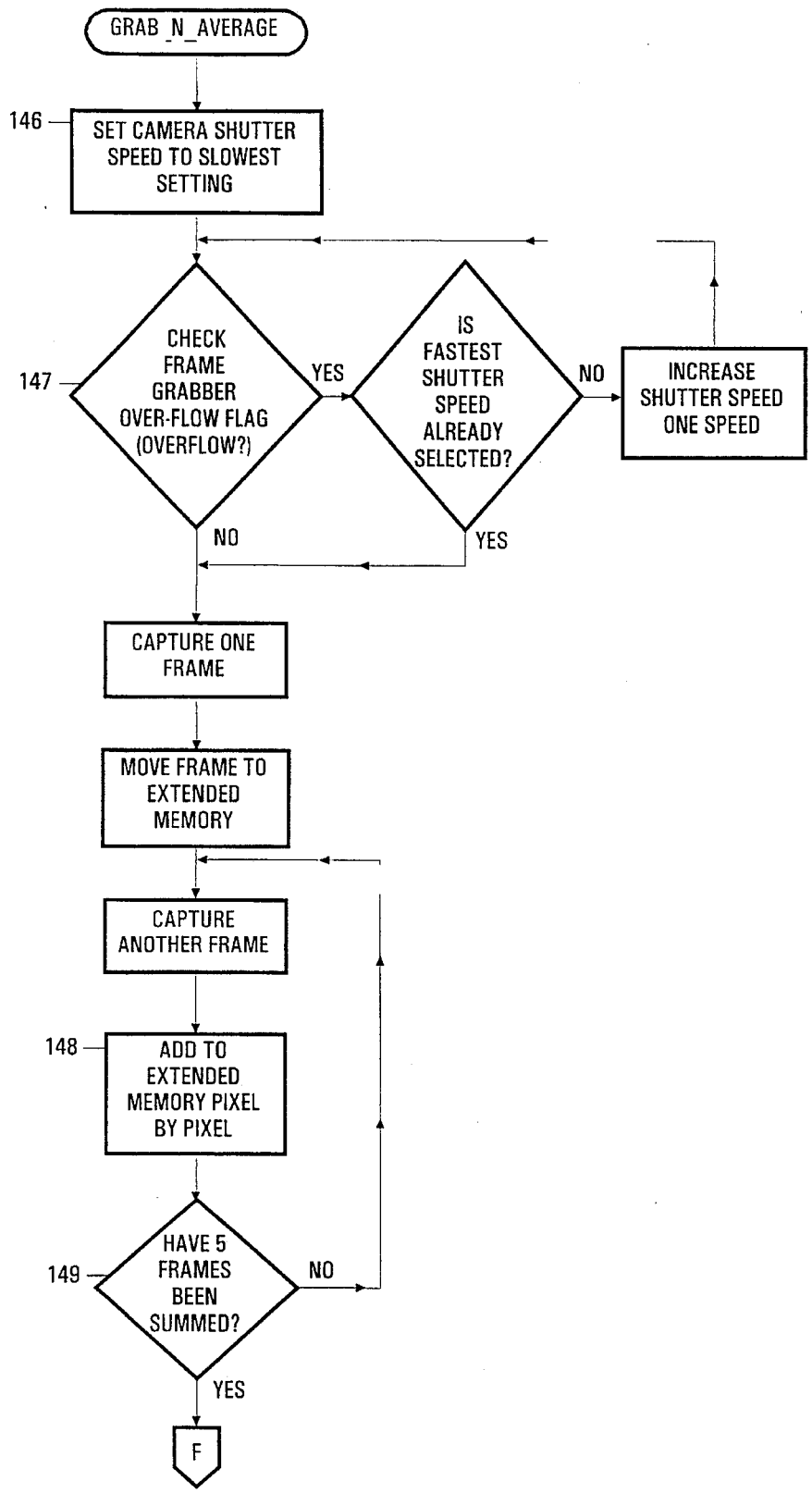
Figure 5I:
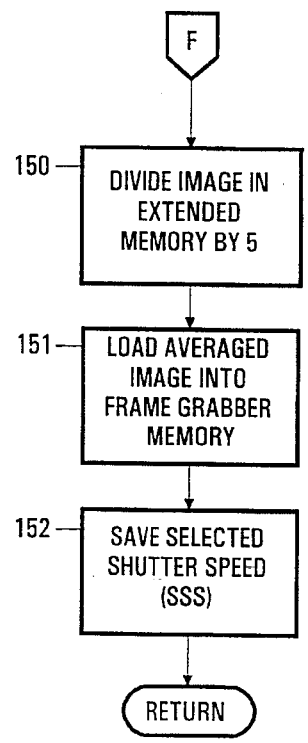
Figure 5J:
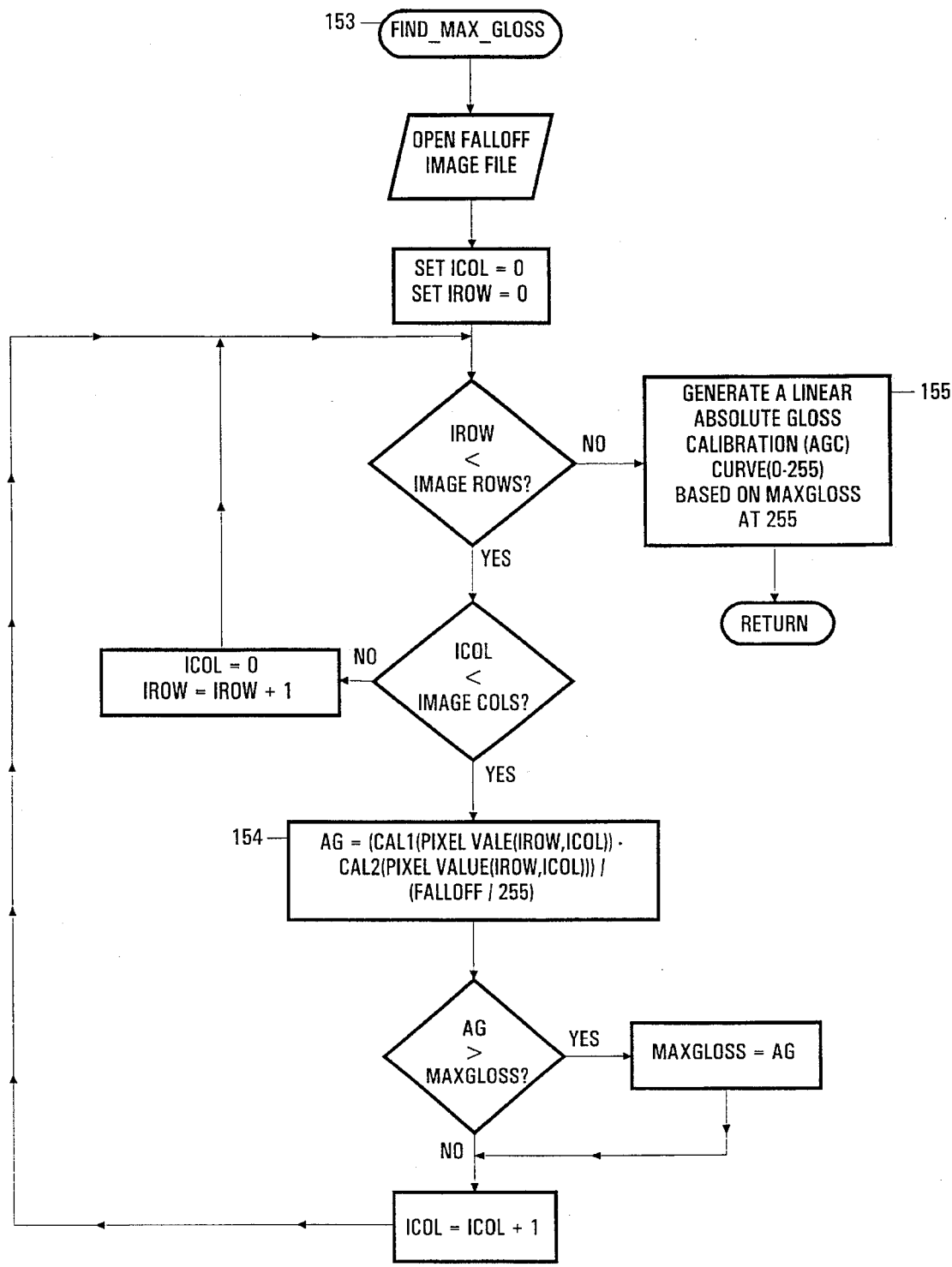
Figure 5K:
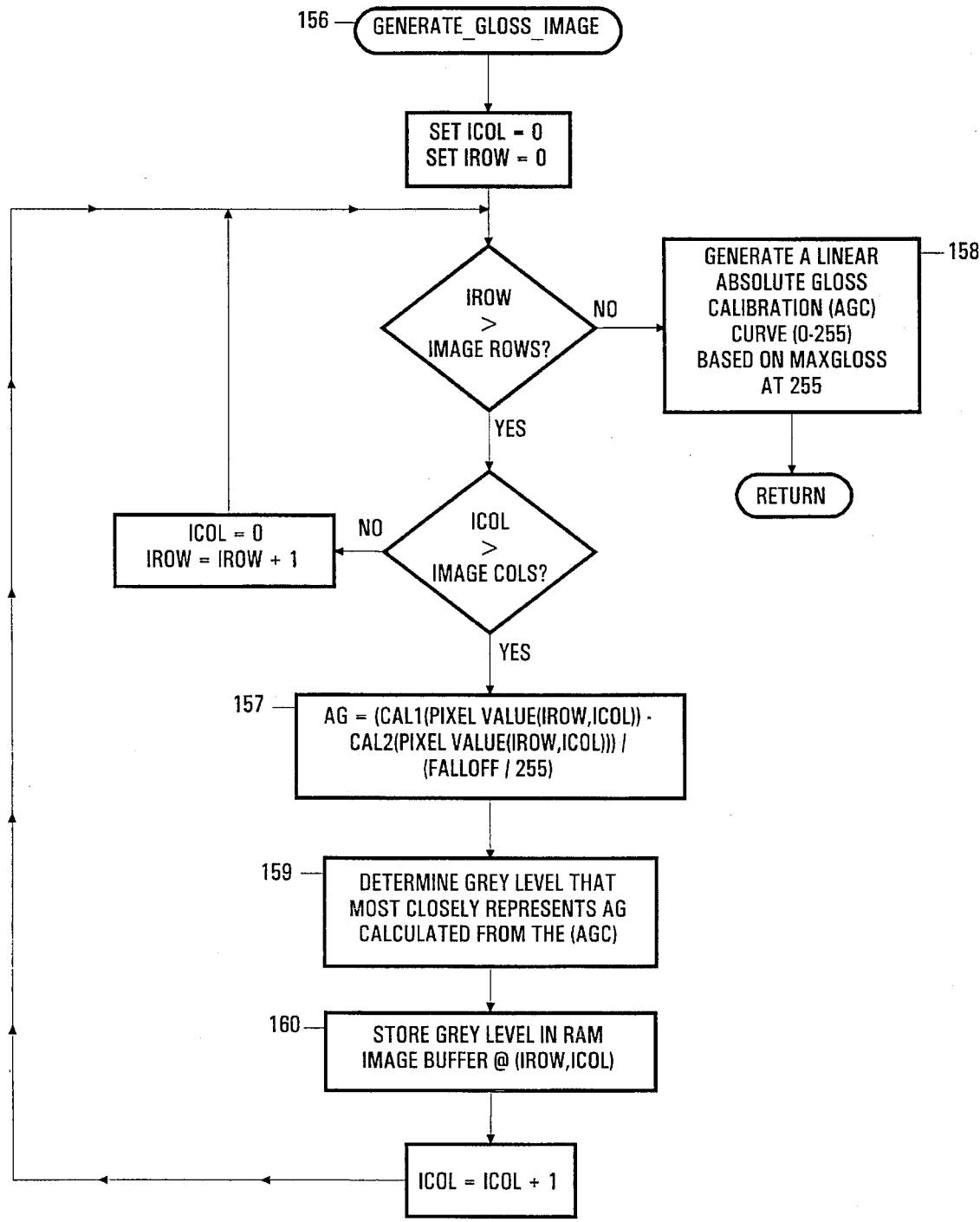
Figure 5I:
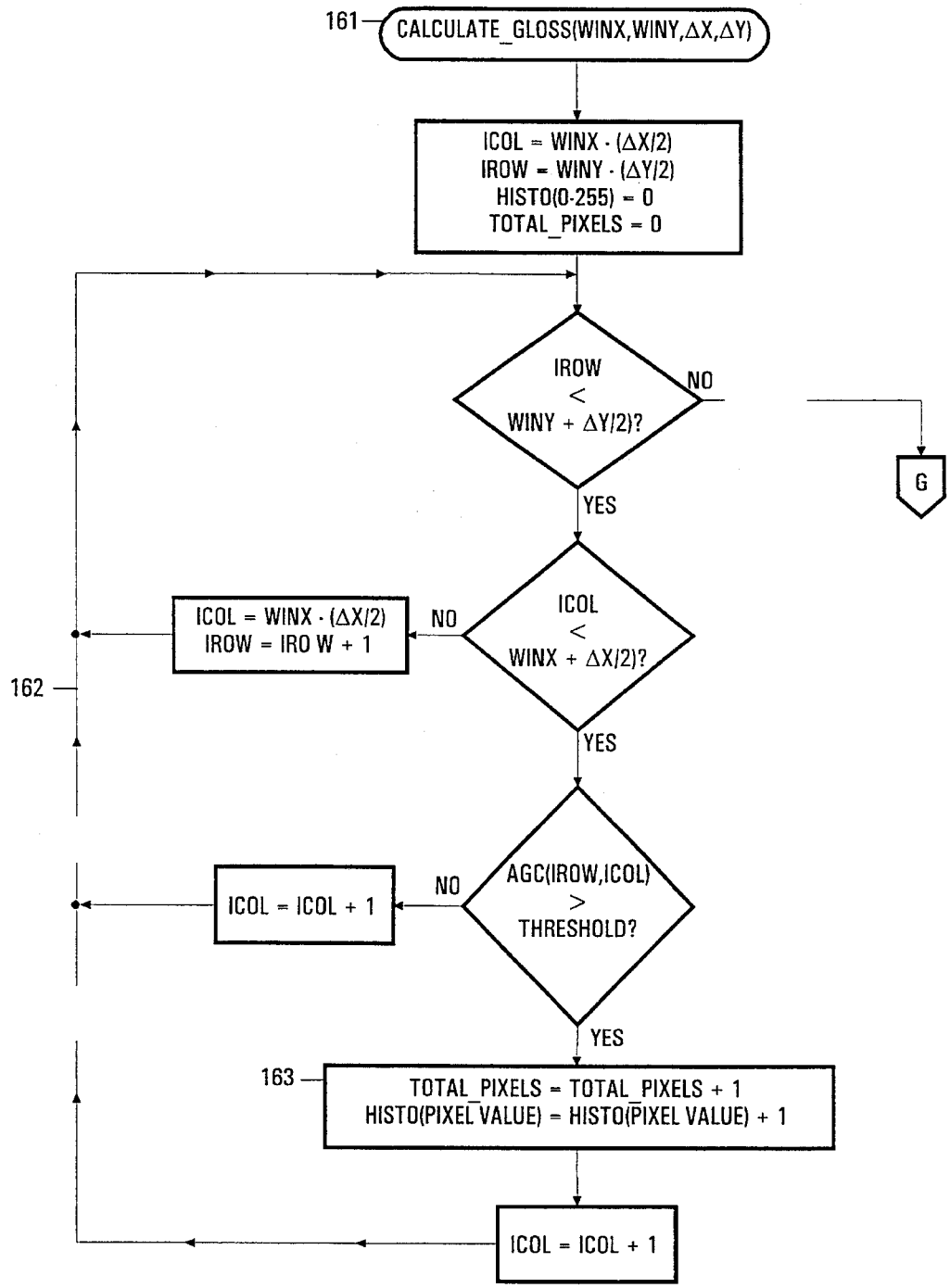
Figure 5M:
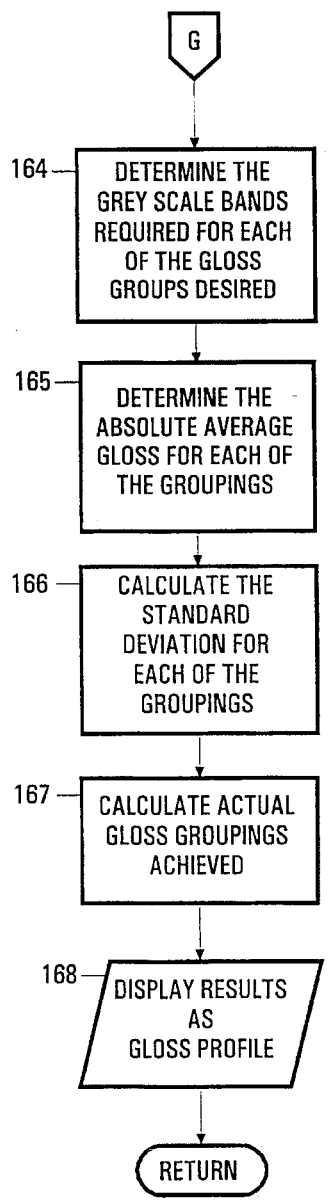
Figure 5N:
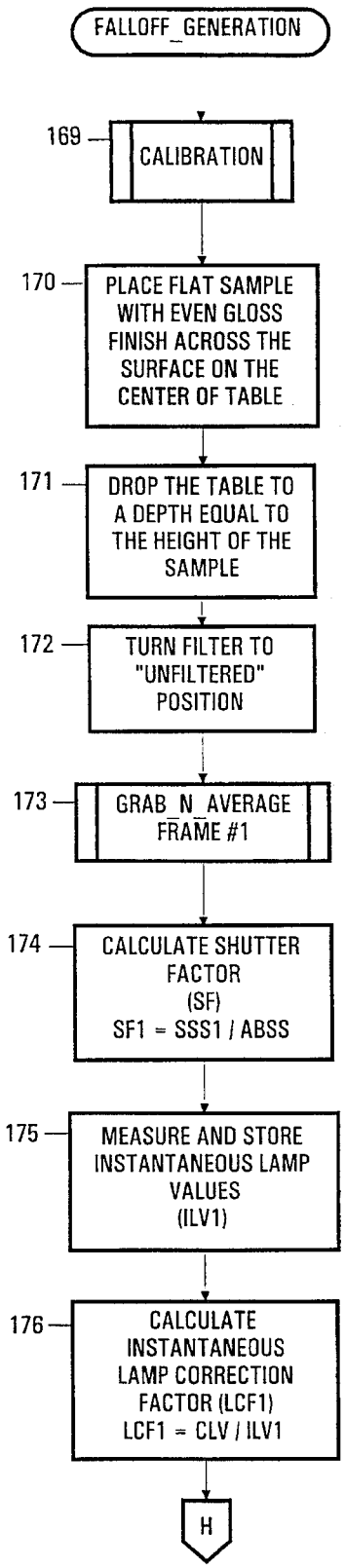
Figure 5O:
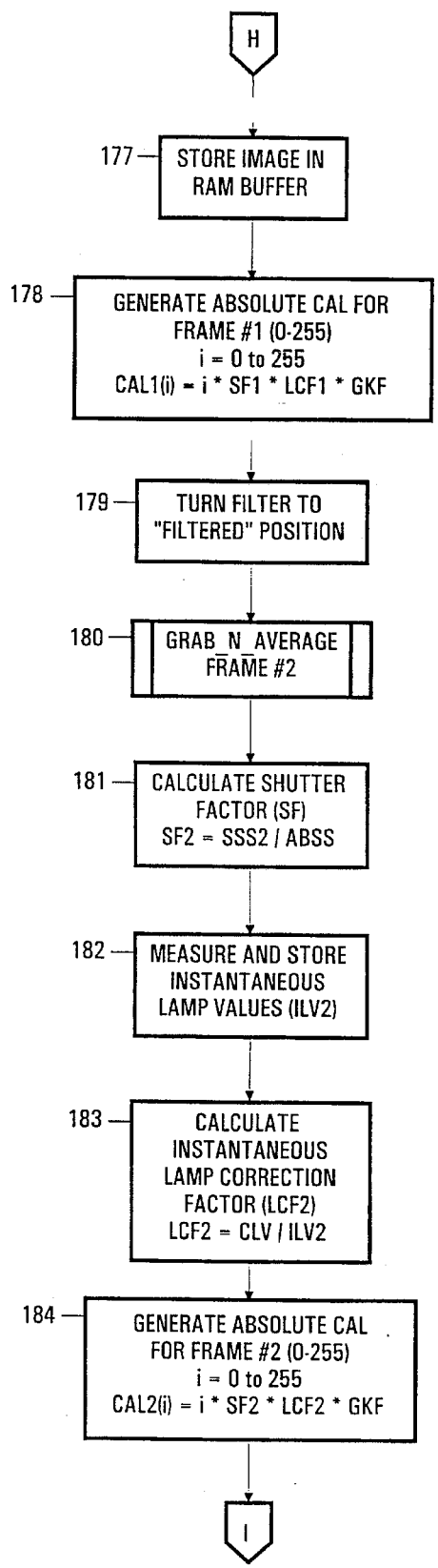
Figure 5P:
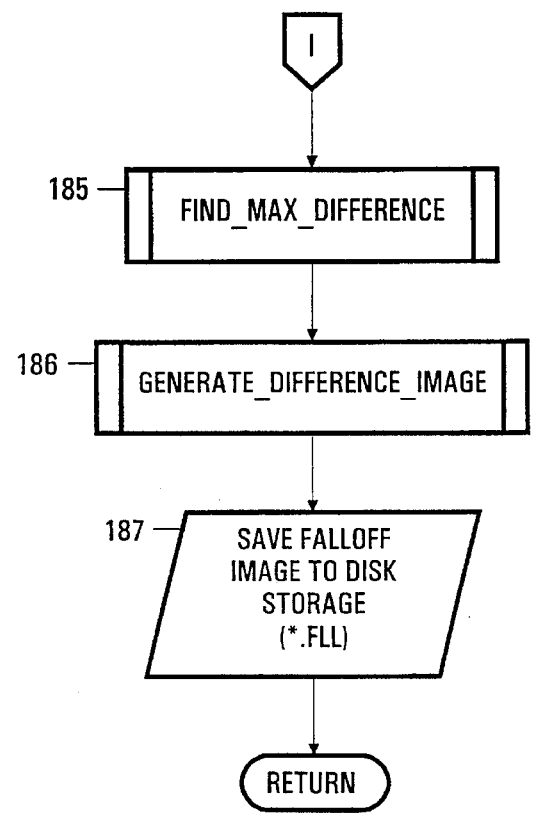
Figure 5Q:
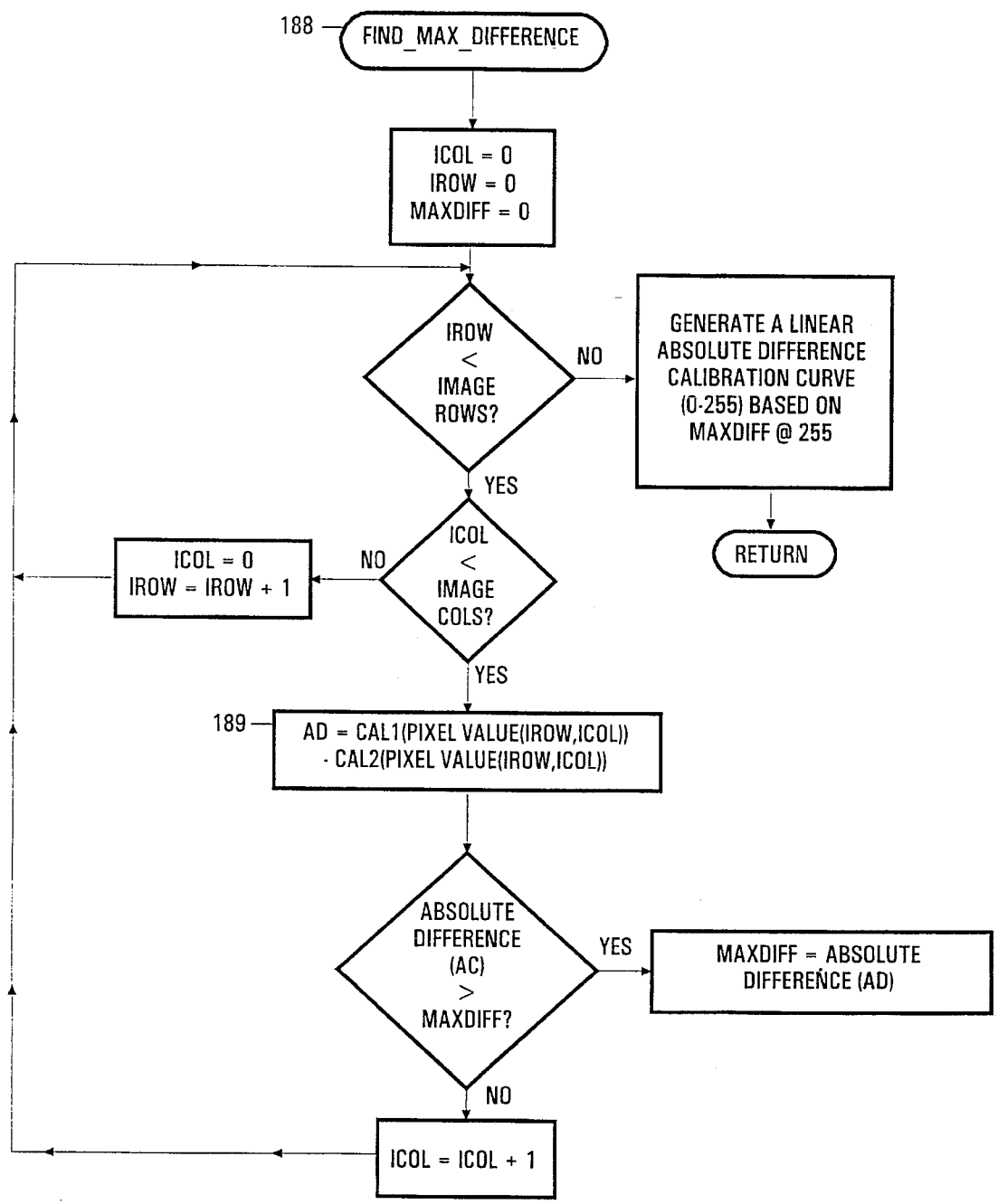
Figure 5R:
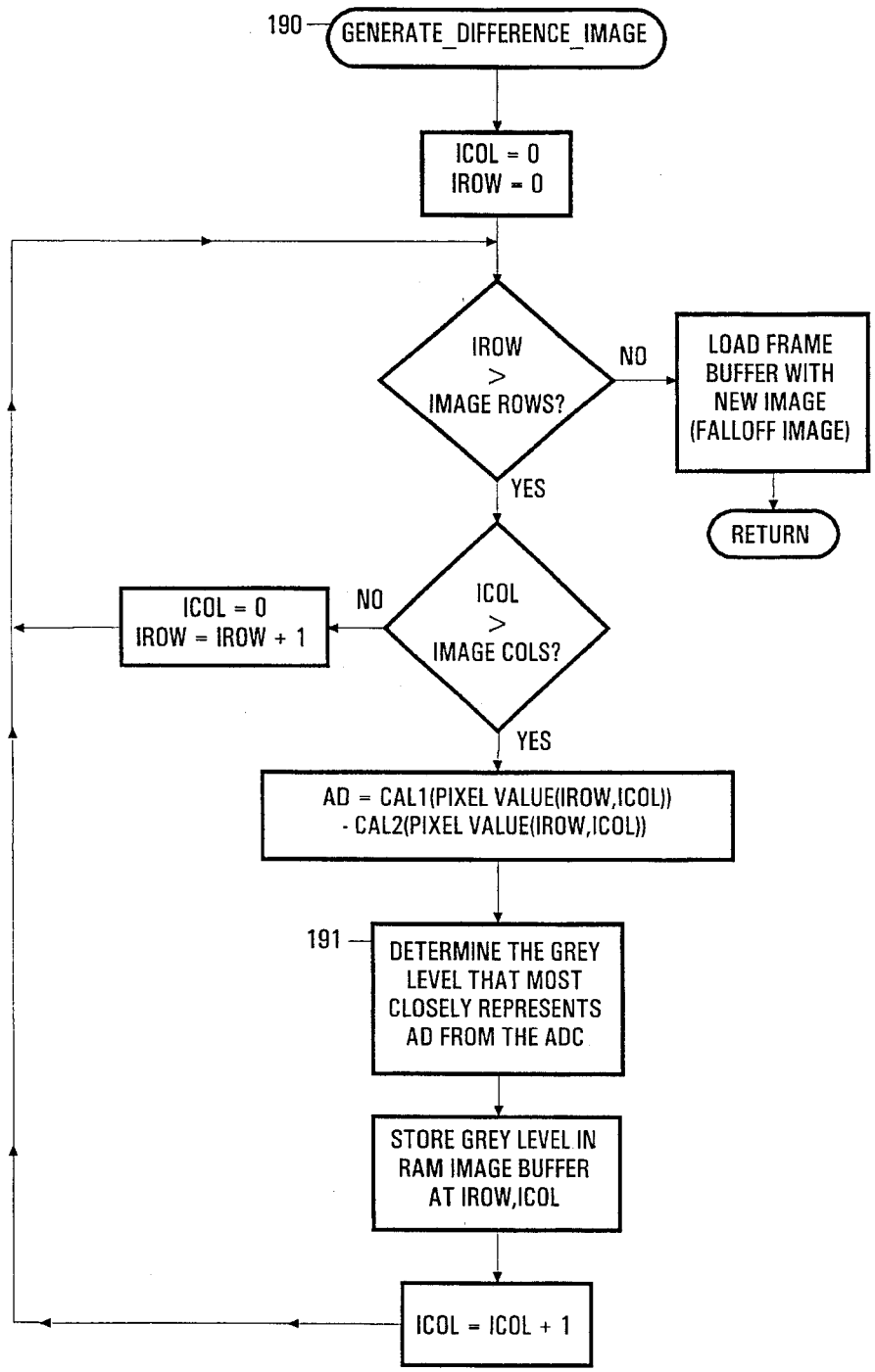
Figure 6:
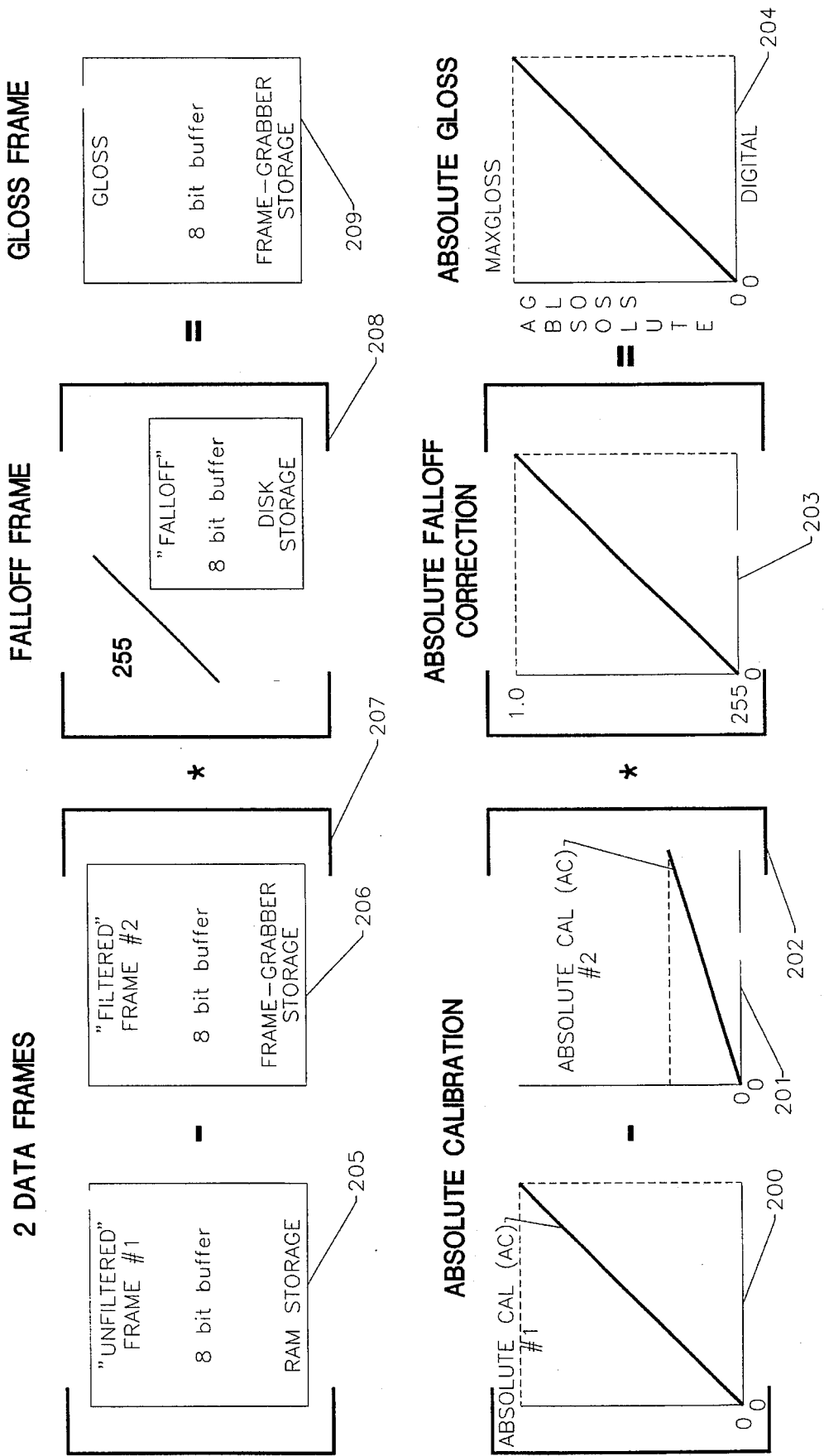
FIG. 6 is a pictorial representation of the calibration and gloss analysis routines performed by the program of FIG. 5.

The flow diagrams shown in FIG. 5, represent the procedural flow used in acquiring frames and image processing methods followed by statistical grouping used to fully generate a gloss image and the use of the image in measuring gloss. FIG. 6 illustrates the "GLOSS IMAGE" development process steps and all its parameters.

In the following description of the flowchart of FIGS. 5a–5r the reference numerals 100, etc. refer to the flowchart blocks shown in FIG. 5. The system must be calibrated 100 before any measurements can be made. Calibration establishes a baseline operating environment and a Gloss K-Factor used to calibrate the system relative to a gloss reference plate.

The sample to be measured is placed 101 in the center of the table 16. The user drops 102 the table 16 an amount equal to the mean height of the sample in order to preserve the 60 degree measuring geometry required for a sample containing an index of refraction of approximately 1.7.

The polarizing filter 20 is turned 103 such that its polarizing axis is vertical allowing the perpendicular component to shine through the filter. This position is referred to as "UNFILTERED". The GRAB-N-AVERAGE routine is called 104 in order to capture frame #1.

The Shutter-Factor (SF1) is calculated 105 for frame #1. This factor is used to compensate the Absolute Calibration Curve for shutter speed changes.

$$SF1 = SSS1/ABSS$$

where:

SF1=Shutter-Factor for frame #1

SS1=Selected Shutter Speed (1/sec)

ABSS=Absolute Shutter Speed (1/sec)

The Instantaneous Lamp Values (ILV1) is measured and stored 106. The Instantaneous Lamp Correction Factor (LCF1) is required 107 in order to correct for lamp intensity variations since calibration time.

$$LCF1 = CLV/ILV1$$

where:

LCF1=Lamp Correction Factor for frame #1

CLV=Calibration Lamp Values

ILV1=Instantaneous Lamp Values for frame #1

Frame #1 is stored 108 in computer RAM for later processing. An absolute calibration curve is saved 109, 200 along with the image. This curve is generated using the following equation.

$$CAL1(i) = i*SF1*LCF1*GKF$$

where:

SF1=Shutter Factor for frame #1

LCF1=Lamp Correction Factor for frame #1

GKF=Gloss K-Factor i=varies from 0 to 255

CAL1=Absolute Cal curve

The polarizing filter 22 is turned 110 such that its polarizing axis is horizontal NOT allowing the specular reflections to shine through the filter. This position is referred to as "FILTERED". The GRAB-N-AVERAGE routine is called 111 in order to capture frame #2.

The Shutter-Factor (SF2) is calculated 112 for frame #2. This factor is used to compensate the Absolute Calibration Curve for shutter speed changes.

$$SF2 = SSS2/ABSS$$

where:

SF2=Shutter-Factor for frame #2

SSS2=Selected Shutter Speed (1/sec)

ABSS=Absolute Shutter Speed (1/sec)

The Instantaneous Lamp Values (ILV1) is measured and stored 113. The Instantaneous Lamp Correction Factor (LCF1) is required 114 in order to correct for lamp intensity variations since calibration time.

$$LCF2 = CLV/ILV2$$

where:

LCF2=Lamp Correction Factor for frame #2

CLV=Calibration Lamp Values

ILV1=Instantaneous Lamp Values for frame #2

An absolute calibration curve is saved along with the image. This curve is generated 115, 201 using the following equation.

$$CAL2(i) = i * SF2 * LCF2 * GKF$$

where:

SF2=Shutter Factor for frame #2

LCF2=Lamp Correction Factor for frame #2

GKF=Gloss K-Factor i=varies from 0 to 255

CAL2=Absolute Cal curve

The FIND-MAX-GLOSS routine is used 116 to subtract frame #2 from frame #1 202 on an absolute pixel by pixel basis and correct for falloff using the falloff image file 203 (see FIG. 6). The maximum value (MAXGLOSS) is retained in order to properly digitize the new gloss image using the maximum dynamic range of the system. The Absolute Pixel Values are calculated using the following equation.

$$\text{Absolute-Gloss } (AG) = \frac{CAL1(\text{frame\#1 pixel}) - CAL2(\text{frame \#2 pixel})}{(\text{Falloff pixel value} / 255)}$$

where:

AG=Absolute Gloss for a pixel located at irow, icol

CAL1=Absolute Cal curve for frame #1

CAL2=Absolute Cal curve for frame #2

FALLOFF PIXEL VALUE=Digital pixel value for the pixel located at irow, icol

MAXGLOSS is used to generate an Absolute Gloss Calibration curve 204. The curve is linear from 0 to MAX-GLOSS stored in a 256 level look-up-table. The entire image is recalculated again in order to digitize 117 the new gloss image based on a digital level of 255 for MAXGLOSS. This is done within a routine called GENERATE-GLOSS-IM-AGE. This image is then loaded back within the frame grabber card's memory. This image is called the "GLOSS" image because it only contains specular reflections at this point.

Gloss calculations can now be performed on the "GLOSS" image. The calculation is done 118 within a user specified rectangular window however the actual calculation can be done over any portion of the image. The user must specify a window location (Winx,Winy) and a window size (Deltx,Delty).

The gloss calculation is done 119 within the CALCU-LATE-GLOSS routine. This calculation groups the brightest pixels (i.e. most gloss) into user specified 8 groupings plus 100%. Within each of these groupings, the statistical absolute gloss average and standard deviation is calculated. The Absolute Average Gloss values for each of the specified group sizes is referred to as the "GLOSS PROFILE". This gloss profile is a direct measure of the samples gloss profile or mirror like quality.

Calibration establishes a baseline operating point in which all subsequent operating points are corrected against; and establishes an overall Gloss K-Factor (GKF) value. The GKF is used to calibrate the gloss hardware to a baseline reference plate. The following describes the calibration flow.

The gloss meter measures samples relative to a calibration reference plate. This reference plate is made of black polished construction grade glass. Its dimensions are approximately 4" square and ¼" thick. This reference plate is placed 120 on the sample table. The sample table is 121 dropped ¼" in order preserve the 60 degree measuring geometry used for samples with an index of refraction of approximately 1.7. The user inputs 122 the Gloss Reference plate value found on the back of the plate.

The light source is turned 123 off in order for the system to measure the Black Level Offset (BLO). This offset is needed in order to truly reflect the hardware's (camera/frame grabber) digitizing characteristics. The GRAB-N-AVER-AGE routine is used 124 to grab 5 frames and average them. An 11×11 pixel portion of the averaged image located in the center of the field is used 125 to determine BLO. BLO is set to the average digital level within this box. The light source is turned back on 126 and the input look-up-table is loaded 127 linearly from BLO to 255 with values from 0 to 255.

The polarizing filter is turned 128 such that its polarizing axis is vertical allowing the specular reflections to shine through the filter. This position is referred to as "NFIL-TERED". The GRAB-N-AVERAGE routine is called 129. The Shutter-Factor (SF1) is calculated 130 for frame #1. This factor is used to compensate the absolute gloss calibration curve for the changes in shutter speed from the absolute shutter speed.

$$\text{Shutter-Factor (SF)} = SSS1/ABSS$$

where:

SSS1=Selected Shutter Speed (frame #1)

ABSS=Absolute Shutter Speed

The light source 12 is measured 131 by a respective photodiode 54 pointing to each of the four fluorescent lamps 48 contained within the light source. Any changes within the light source must be accounted for in the measuring algorithm. Calibration establishes an operating point at which all corrections must take place. Therefore the lamp intensity values are stored and called Calibration Lamp Values (CLV) to be used for later measurement lamp corrections.

The Instantaneous Lamp Correction Factor is set 132 to 1.00 for calibration because the current lamp values are used as a baseline and no correction is needed at this point.

Frame #1 205 is stored 133 in a RAM buffer.

An Absolute Calibration for Frame #1 is calculated 134 based on the Shutter Speed Factor.

$$CAL1[i] = i * SF1 * LCF$$

where

SF1=Shutter-Factor Frame #1

LCF=Lamp Correction Factor is 1.0 at calibration time

CAL1=Absolute calibration for Image #1 i=Varies from 0 to 255

The polarizing filter 22 is turned 135 such that the polarizing axis is horizontal, thus not allowing the specular reflections to shine through the filter. This position is referred to as "FILTERED". The GRAB-N-AVERAGE routine is called 136. The Shutter-Factor (SF2) is calculated 137 for frame #2. This factor is used to compensate the absolute gloss calibration curve for the change in shutter speed.

$$\text{Shutter-Factor (SF)} = SSS2/ABSS$$

where:

SSS2=Selected Shutter Speed (frame #2)

ABSS=Absolute Shutter Speed

The light source 12 is measured 138 by a respective photodiode 54 pointing to each of the four fluorescent lamps 48 contained within the light source. Any changes within the light source must be accounted for in the measuring algorithm. Calibration establishes an operating point at which all corrections must take place. Therefore the lamp intensity values are stored and called Calibration Lamp Values (CLV).

The Instantaneous Lamp Correction Factor is set 139 to 1.00 for calibration because the current lamp values are used as a baseline and no correction is needed at this point.

Frame #2 206 is stored 140 in a frame grabber buffer.

An Absolute Calibration for Frame #2 is calculated 141 based on the Shutter Speed Factor.

$$CAL1[i] = i * SF1 * LCF$$

where:

SF1=Shutter-Factor Frame #1
LCF=Lamp Correction Factor is 1.0 at calibration time
CAL1=Absolute calibration for Image #1
i=Varies from 0 to 255

The falloff image file is opened 208. The falloff image is used to compensate pixel values in order to flatten out the brightness field. FIND-MAX-GLOSS routine is called 142 in order to determine the maximum absolute gloss value found for any pair of pixels. The FIND-MAX-GLOSS routine is used to subtract frame #2 from frame #1 on an absolute pixel by pixel basis 207 and is corrected for falloff phenomena. The equation used to determine Absolute Gloss (AG) and is calculated on a pixel pair by pixel pair basis and the maximum gloss value (MAXGLOSS) is stored 209.

$$\text{Absolute-Gloss }(AG) = \frac{CAL1(\text{frame\#1 pixel}) - CAL2(\text{frame \#2 pixel})}{(\text{Falloff pixel value} / 255)}$$

where:

AG=Absolute Gloss for a pixel located at irow, icol
CAL1=Absolute Cal curve for frame #1
CAL2=Absolute Cal curve for frame #2
FALLOFF PIXEL VALUE=digital pixel value for the pixel located at irow,icol MAXGLOSS is used to generate an Absolute Gloss Calibration curve. The curve is linear from 0 to MAX-GLOSS stored in a 256 level look-up-table. The entire image is recalculated 143 again in order to digitize the new gloss image based on a digital level of 255 for MAXGLOSS. This is done in the routine called GENERATE-GLOSS-IMAGE.

This image is loaded back into the frame grabber cards memory. This image is called a "GLOSS" image 207 because it only contains specular reflections at this point.

A 100% Absolute Gloss Average is calculated 144. This means that all the pixels above the user specified threshold level is averaged on an absolute basis.

The Gloss K-Factor can now be calculated 145 by the following equation.

$$\text{Gloss }K\text{-Factor }(GKF) = \frac{\text{Gloss Reference Plate Value }(GRPV)}{100\% \text{ Absolute Gloss Average }(AGA)}$$

where:

GKF=Gloss K-Factor is used to calibrate the system to the reference plate.
GRPV=Gloss Reference Plate Value is entered by the user and found on the back of the reference plate.
AGA=Absolute Gloss Average of 100% grouping within the 11×11 pixel area in the center of the display.

Calibration is now complete. Again, the reason for calibrating is to establish a baseline operating environment in which all subsequent measurements will be compared and compensated against and to calculate the GKF which is needed to correlate the entire system to the baseline point referred to as the calibration reference plate.

The following describes the method used to minimize any digitization variances during acquisition of frames 1 and 2.

The first step is to find the proper shutter speed to guarantee linear camera operation 146, 147. The shutter speed is sequentially changed from slowest to fastest until the frame grabber OVER-FLOW flag is not set.

GRAB-N-AVERAGE routine is used to grab 5 frames sequentially and sum 148 the frames on a pixel by pixel basis. The frames are acquired using an 8 bit digital frame grabber board. Each frame acquired is summed 148 to the temporary image stored in extended memory. This summing continues until 5 frames have been acquired 149. The temporary image is then divided 150 by 5 in order to achieve the averaged image. The averaged frame residing in extended memory is then loaded 151 back into the digital frame grabber memory. The selected shutter speed (SSS) is saved 152 for absolute calibration generation.

This technique is used to minimize both the CCD sensor and A/D conversion variances inherent to a digital frame grab board.

The following describes the methods used to find the maximum gloss value in order to determine properly redigitize the gloss image.

FIND-MAX-GLOSS routine 153 is used to scan a frame pixel by pixel in order to find the maximum absolute gloss found between frame #1 pixel and frame #2 pixel. The difference is corrected for falloff and Absolute Gloss (AG) is calculated 154 by using the following equation.

$$\text{Absolute Gloss }(AG) = \frac{CAL1(\text{frame\#1 pixel}) - CAL2(\text{frame \#2 pixel})}{(\text{Falloff pixel value} / 255)}$$

where:

AG=Absolute Gloss for a pixel located at irow, icol
CAL1=Absolute Cal curve for frame #1
CAL2=Absolute Cal curve for frame #2
FALLOFF PIXEL VALUE=digital pixel value for the pixel located at irow, icol At the completion of FIND-MAX-GLOSS the maximum gloss was calculated 159 and retained in order to generate a linear calibration 155 based on that retained maximum value. The following describes the method used to generate the gloss image based on the maximum absolute gloss value.

GENERATE-GLOSS-IMAGE routine 156 is used to create a gloss image consisting of the absolute difference 157 between frame #1 and frame #2 with falloff compensation.

The entire image is scanned in the same manner as FIND-MAX-GLOSS routine. In addition to that methodology each absolute calculation is looked up 159 in the Absolute Gloss Calibration curve to determine the proper grey scale value to which that pixel will be set. The absolute calibration curve is generated 158 base on the MAXGLOSS calculated.

A gloss image has been created and digitized based on a linear Absolute Gloss Calibration curve and can directly be used to measure gloss.

The following method is used to calculate gloss from the "Gloss Image" previously generated.

CALCULATE-GLOSS routine 161 is used to calculate a gloss profile from a "GLOSS" image using the Absolute Gloss Calibration curve (AGC). A gloss profile is the average gloss for each of 8 groupings plus the 100% group. Each group represents the brightest n % of the pixels above the threshold. The size of "n" is user specified and the user can specify up to 8 groups with the 9th group being reserved for the 100% group. For example, a group size of 10% means ten percent of the brightest (glossiest) pixels within the gloss window above the threshold. Those and only those pixels within each group are included in an Absolute Average Gloss (AAG) calculation for that group. Standard Deviation is also calculated for each group. The "Threshold" is user specified and allows for the elimination of either background or shadowed areas within the field of view based solely on amplitude.

The image within the defined window is scanned 162 and all pixels above the threshold is summed and referred to as Total Pixels. At the same time, the histogram representing the pixels within the window is created 163. Each pixel's value is used as an index into the histogram array and a value of 1 is summed for every pixel above the threshold. A graphic representation of the histogram is available on the computer display.

The actual groupings are made 164 by summing the pixels within the histogram starting at 255 until the summed pixels represent on a percentage of the whole basis as close as possible to the ideal or user specified group size. Those pixels are averaged 165 on an absolute basis and standard deviation 166 is also calculated.

The resulting Gloss Profile is displayed and a typical display is shown below.

| % Ideal | % Actual | Avg Gloss | Std Dev |
|---------|----------|-----------|---------|
| 5       | 5        | 100       | 5       |
| 10      | 10       | 95        | 8       |
| 15      | 16       | 90        | 12      |
| 20      | 19       | 84        | 16      |
| 25      | 25       | 80        | 19      |
| 30      | 29       | 75        | 21      |
| 40      | 42       | 66        | 28      |
| 50      | 51       | 56        | 35      |
| 100     | 100      | 50        | 37      |

The above example shows the user specified groupings (% Ideal) shown in the left column. The actual achieved groupings 167 (% Actual) is shown in the second column. The % means percent of the total pixels above the threshold. The (Avg Gloss) and (Std Dev) columns are the average absolute gloss and standard deviation respectfully. The above display represents a "Gloss Profile Summary" 168.

The following method flow is used to generate a falloff correction image.

The system must be calibrated 169 before any measurements can be made. Calibration establishes a baseline operating environment and a Gloss K-Factor used to calibrate the system relative to the gloss reference plate.

The sample to be used for falloff correction 170 should be constructed of the same material as the sample(s) being measured. It must be flat and as even a gloss as possible. The sample must fill the display in order to generate a full display falloff correction image. The user must drop the table 16 an amount equal to the height of the sample in order to preserve the 60 degree measuring geometry required for a sample containing an index of refraction of approximately 1.7.

The polarizing filter 20 is turned 172 such that its polarizing axis is vertical allowing the specular reflections to shine through the filter. This position is referred to as "UNFILTERED". The GRAB-N-AVERAGE routine is called 173.

The Shutter-Factor (SF1) is calculated 174 for frame #1. This factor is used to compensate the Absolute Calibration Curve for shutter speed changes.

$$SF1 = SSS1/ABSS$$

where:

SF1=Shutter-Factor for frame #1

SSS1=Selected Shutter Speed (1/sec)

ABSS=Absolute Shutter Speed (1/sec)

The Instantaneous Lamp Values (ILV1) is measured and stored 175. The Instantaneous Lamp Correction Factor (LCF1) is required in order to correct for lamp intensity variations since calibration time.

$$LCF1 = CLV/ILV1$$

where:

LCF1=Lamp Correction Factor for frame #1

CLV=Calibration Lamp Values

ILV1=Instantaneous Lamp Values for frame #1

The image grabbed and averaged is stored 177 in computer RAM for later processing. Along with the image a absolute calibration curve is saved. This curve is generated 178 using the following equation.

$$CAL1(i) = i*SF1*LCF1*GKF$$

where:

SF1=Shutter Factor for frame #1

LCF1=Lamp Correction Factor for frame #1

GKF=Gloss K-Factor i=varies from 0 to 255

CAL1=Absolute Cal curve for frame #1

The polarizing filter 22 is turned 179 such that its polarizing axis is horizontal, thus not allowing the specular reflections to shine through the filter. This position is referred to as "FILTERED". The GRAB-N-AVERAGE routine is called 180.

The Shutter-Factor (SF2) is calculated 181 for frame #2. This factor is used to compensate the Absolute Calibration Curve for shutter speed changes.

$$SF2 = SSS2/ABSS$$

where:

SF2=Shutter-Factor for frame #2

SSS2=Selected Shutter Speed (1/sec)

ABSS=Absolute Shutter Speed (1/sec)

The Instantaneous Lamp Values (ILV1) is measured and stored 182. The Instantaneous Lamp Correction Factor (LCF1) is required 183 in order to correct for lamp intensity variations since calibration time.

$$LCF2 = CLV/ILV2$$

where:

LCF2=Lamp Correction Factor for frame #2

CLV=Calibration Lamp Values

ILV1=Instantaneous Lamp Values for frame #2

The image grabbed and averaged is stored in computer RAM for later processing. Along with the image a absolute calibration curve is saved. This curve is generated 184 using the following equation.

$$CAL2(i) = i*SF2*LCF2*GKF$$

where:

SF2=Shutter Factor for frame #2

LCF2=Lamp Correction Factor for frame #2

GKF=Gloss K-Factor i=varies from 0 to 255

CAL2=Absolute Cal curve for frame #2

The FIND-MAX-DIFFERENCE routine 185 is used to subtract frame #2 from frame #1 on an absolute pixel by pixel basis. No correction falloff file is used to generate a falloff correction image. This image must reflect the actual falloff phenomena in order to correct any subsequent measurements. The maximum value (MAXDIFF) is retained in order to properly digitize the new gloss image using the maximum dynamic range of the system. The Absolute Pixel Values are calculated using the following equation.

$$\text{Absolute-Difference (AD)} = \text{CAL1(fr\#1 pixel)} - \text{CAL2(fr\#2 pixel)}$$

where:
AD=Absolute Difference for a pixel located at irow, icol
CAL1=Absolute Cal curve for frame #1
CAL2=Absolute Cal curve for frame #2

MAXDIFF is used to generate an Absolute Difference Calibration (ADC) curve. The curve is linear from 0 to MAXDIFF stored in a 256 level look-up-table. The entire image is recalculated again in order to digitize the new difference image based on a digital level of 255 for MAXDIFF. This is done within a routine 186 called GENERATE-DIFFERENCE-IMAGE. This image is then loaded back within the frame grabber card's memory. This image is called the "FALLOFF" image because it contains the exact falloff mapping across the image. This mapping is used directly on a pixel by pixel basis to correct all absolute gloss calculations.

This falloff image is stored 187 to disk storage to be used whenever samples of the same material are measured at a later time.

The following method flow is used to find the maximum difference when generating an image to be used for falloff correction.

FIND-MAX-DIFFERENCE routine 188 is used to scan a frame pixel by pixel in order to find the maximum absolute difference found between frame #1 pixel and frame #2 pixel. The Absolute Difference 189 (AD) is calculated by using the following equation.

$$\text{Absolute Difference (AD)} = \text{CAL1(fr \#1 pixel)} - \text{CAL2(fr \#2 pixel)}$$

where:
AD=Absolute Difference for a pixel located at irow, icol
CAL1=Absolute Cal curve for frame #1
CAL2=Absolute Cal curve for frame #2

The following method flow is used to generate a difference image used for falloff correction.

GENERATE-DIFFERENCE-IMAGE routine 190 is used to create a falloff image consisting solely of the absolute difference between frame #1 and frame #2 without falloff correction.

The entire image is scanned in the same manner as FIND-MAX-DIFFERENCE routine. In addition to that methodology each absolute calculation is looked up in the Absolute Difference Calibration curve to determine the proper grey scale value to which that pixel will be set.

A pure difference image has been created and digitized based on a linear Absolute Difference Calibration curve and is used for falloff correction.

The foregoing detailed description has been given for clearness of understanding only, and no unnecessary limitations should be understood therefrom, as modifications will be obvious to those skilled in the art.

We claim:

1. A method of optically measuring the gloss of an irregularly shaped object using a specular reflection component of light reflected from the irregularly shaped object, said specular reflection component including a perpendicular polarization component, and said gloss being defined in terms of a capacity of a surface to reflect more light in a specular direction as compared to other directions and said gloss being measured by the magnitude of the perpendicular polarization component, the method of optically measuring the gloss of the irregularly shaped object to provide a gloss image of the irregularly shaped object comprising the steps of:

illuminating the irregularly shaped object with a light source providing an unpolarized, broad band light directed at an oblique angle to the irregularly shaped object;

deriving essentially only the magnitude of the perpendicular polarization component of the specular reflection component of polarized light from the irregularly shaped object while excluding light reflected in other directions to provide a derived gloss image of the irregularly shaped object, said derived gloss image including a plurality of gloss image pixels having a gloss level;

obtaining an absolute average gloss image of the irregularly shaped object from the derived gloss image, including;

statistically grouping the gloss image pixels into a plurality of groupings according to the associated gloss levels thereof; and averaging the brightest predetermined N percent of the gloss image pixels together within each of the groupings to obtain said absolute average gloss image of the irregularly shaped object corresponding to said optically measured gloss.

2. The method of claim 1, including the step of calculating the standard deviation for each of the groupings.

3. The method of claim 1, including correcting the gloss image for image fall-off characteristics.

4. The method of claim 1, including monitoring the intensity of the light source.

5. The method of claim 4, including correcting the derived gloss image of the object in response to the monitored light source intensity.

6. The method of claim 1, including establishing a reference gloss image factor value for a reference plate having a known reference value by deriving the reference gloss image factor using the reference plate as the object.

7. The method of claim 6, including establishing a black level offset reference value.

8. The method of claim 1, wherein the averaging of the gloss image pixels is with respect to a brightness threshold.

9. The method of claim 1, including displaying the resulting gloss image of the irregularly shaped object.

10. Apparatus for optically measuring the gloss of an irregularly shaped object using a specular reflection component of light reflected from the irregularly shaped object, said specular refection component including a perpendicular polarization component, and said gloss being defined in terms of a capacity of a surface to reflect more light in a specular direction as compared to other directions and said gloss being measured by the magnitude of the perpendicular polarization component, the apparatus for optically measuring the gloss of the irregularly shaped object to provide a gloss image of the irregularly shaped object comprising:

a light source providing an unpolarized, broad band light for illuminating the irregularly shaped object with unpolarized light directed at an oblique angle to the irregularly shaped object;

means for deriving essentially only the magnitude of the perpendicular polarization component of the specular reflection component of polarized light from the irregularly shaped object while excluding light reflected in other directions to provide a derived gloss image of the irregularly shaped object, said derived gloss image including a plurality of gloss image pixels having a gloss level;

means for obtaining an absolute average gloss image of the irregularly shaped object from the derived gloss image, including;

means for statistically grouping the gloss image pixels into a plurality of groupings according to the associated gloss levels thereof; and means for averaging the brightest predetermined N percent of the gloss image pixels together within each of the groupings to obtain said absolute average gloss image of the irregularly shaped object corresponding to said optically measured gloss.

11. Apparatus according to claim 10, including means for calculating the standard deviation for each of the groupings.

12. Apparatus according to claim 10, including means for correcting the gloss image for image fall-off characteristics.

13. Apparatus according to claim 10, including means for monitoring the intensity of the light source.

14. Apparatus according to claim 13, including means for correcting the derived gloss image of the object in response to the monitored light source intensity.

15. Apparatus according to claim 10, including means for establishing a reference gloss image factor value for a reference plate having a known reference value by deriving the reference gloss image factor using the reference plate as the object.

16. Apparatus according to claim 15, including means for establishing a black level offset reference value.

17. Apparatus according to claim 10, including a table for supporting the object, and means for adjusting the height of the table to maintain an optimum oblique angle for the object corresponding to the object's index of refraction.

18. Apparatus according to claim 17, including a stepper motor and screw drive means coupling the stepper motor to the table for incrementally adjusting the height of the table.

19. Apparatus according to claim 17, including means for incrementally rotating the table to enable gloss measurements of the object in a 360° view of the object.

20. Apparatus according to claim 10, including a plurality of light sources to provide the illumination directed at the object.

21. Apparatus according to claim 20, including a reflector assembly adjacent the plurality of light sources to provide field flattening of the illumination pattern.

22. Apparatus according to claim 20, including a respective photodiode for each of said light sources adapted to monitor the intensity of each light source.

23. Apparatus according to claim 22, including means for correcting the derived gloss image of the object in accordance with the monitored intensity of each light source.

24. Apparatus according to claim 10, wherein the averaging of the gloss image pixels is with respect to a brightness threshold.

25. Apparatus according to claim 10, including means for displaying the resulting gloss image of the irregularly shaped object.

* * * * *

UNITED STATES PATENT AND TRADEMARK OFFICE
CERTIFICATE OF CORRECTION

PATENT NO. : 5,552,890
DATED : September 3, 1996
INVENTOR(S) : FRANK P. NANNA, ET AL.

It is certified that error appears in the above-indentified patent and that said Letters Patent is hereby corrected as shown below:

Col. 6, line 29,   after "broad" insert --band--.

Col. 7, line 29,   after "sensor" insert --76--.

Col. 10, lines 11-12,   delete "'NFILTERED'" and insert --"UNFILTERED"--.

Signed and Sealed this

Fourth Day of March, 1997

Attest:

BRUCE LEHMAN

*Attesting Officer*   Commissioner of Patents and Trademarks